US012435353B2

(12) United States Patent
Durham

(10) Patent No.: US 12,435,353 B2
(45) Date of Patent: Oct. 7, 2025

(54) BIOMARKER ASSAY FOR USE IN MONITORING AUTISM

(71) Applicant: STALICLA SA, Geneva (CH)

(72) Inventor: Lynn Durham, Geneva (CH)

(73) Assignee: STALICLA SA, Geneva (CH)

( * ) Notice: Subject to any disclaimer, the term of this patent is extended or adjusted under 35 U.S.C. 154(b) by 0 days.

(21) Appl. No.: 18/470,985

(22) Filed: Sep. 20, 2023

(65) Prior Publication Data

US 2024/0011071 A1 Jan. 11, 2024

Related U.S. Application Data

(63) Continuation of application No. 16/761,926, filed as application No. PCT/EP2018/080375 on Nov. 6, 2018, now abandoned.

(60) Provisional application No. 62/582,213, filed on Nov. 6, 2017.

(30) Foreign Application Priority Data

Nov. 6, 2017 (EP) .................................... 17200220

(51) Int. Cl.
*C12Q 1/48* (2006.01)

(52) U.S. Cl.
CPC .................................... *C12Q 1/485* (2013.01)

(58) Field of Classification Search
None
See application file for complete search history.

(56) References Cited

U.S. PATENT DOCUMENTS

2008/0124790 A1 5/2008 Yang et al.
2014/0303031 A1 10/2014 Kunkel et al.

FOREIGN PATENT DOCUMENTS

JP 2019-089755 A 6/2019
WO 2013066972 A1 5/2013

OTHER PUBLICATIONS

Lemonnier, E., et al. 2017 Transl Psychiatry 7:e1056 (9 pages). (Year: 2017).*

(Continued)

*Primary Examiner* — Marsha Tsay
(74) *Attorney, Agent, or Firm* — Millen, White, Zelano & Branigan; Ryan R. Pool

(57) ABSTRACT

The present invention relates to protein kinase A (PKA) for use in diagnosing autism spectrum disorder (ASD) phenotype 1 in an ASD patient wherein PKA levels are measured in a sample of the patient and wherein ASD phenotype 1 is diagnosed if the measured levels are lower than PKA levels in an age and sex-matched control sample. Additionally, the present invention relates to PKA for use in monitoring variation in ASD severity in an ASD patient, wherein PKA levels are measured in a sample of the patient and an increase in ASD severity is characterized by a decrease of PKA levels compared to PKA levels measured in previous samples of the patient. The present invention also relates to PKA for use in monitoring efficacy of an ASD treatment in an ASD phenotype 1 patient, wherein PKA levels are measured in a sample of the patient and wherein a positive response to the ASD treatment is characterized by an increase of PKA levels in comparison to baseline PKA levels of the patient prior to treatment. Furthermore, the present invention is directed to methods of diagnosing ASD phenotype 1 as well as kits comprising means to measure PKA levels.

2 Claims, No Drawings

(56) References Cited

OTHER PUBLICATIONS

Chadman, K.K. 2017 Expert Opinion on Drug Discovery 12(12): 1187-1194. (Year: 2017).*
Schaefer, G.B., et al. 2008 Genet Med 10(1): 4-12. (Year: 2008).
Russo, A.J., et al. 2017 Acad J Ped Neonatal 5(3): 555721, pp. 0057-0060. (Year: 2017).
Yasuko Kitagishi et al: 11 Neuron Membrane Trafficking and Protein Kinases Involved in Autism and ADHO 11 , International Journal of Molecular Sciences, vol. 16, No. 2, Jan. 30, 2015 (Jan. 30, 2015), pp. 3095-3115. XP055463562, CH.
Lina Ji et al: "Brain Region-specific Decrease in the Activity and Expression of Protein Kinase A in the Frontal Cortex of Regressive Autism", PLOS One, vol. 6, No. 8, Aug. 31, 2011 (Aug. 31, 2011), p. e23751, XPO55463568, DOI: 10.1371/joumal.phone. 0023751.
Kim Nuytens et al: "Platelets of mice heterozygous for neurobeachin, a candidate gene for autism spectrum disorder, display protein changes related to aberrant protein kinase A activity", Molecular Autism, Biomed Central Ltd, London, UK, vol. 4, No. 1, Nov. 4, 2013, p. 43, XP021168899, ISSN: 2040-2392,001: 10.1186/2040-2392-4-43.
PKA (Protein Kinase A) Colorimetric Activity Kit [retrieved from internet on May 26, 2021] URL: https://www.thermofisher.com/order/catalog/product/EIAPKA#/EIAPKA> published on Mar. 3, 2017.
JP 2020-526315 Yi et al; 2015; Cell, vol. 162, No. 4, pp. 795-807 "An Autism-Linked Mutation Disables Phosphorylation Control of UBE3A".
Barrett et al; 2017; Molecular Autism, vol. 8, p. 42 "Developmental disruption of amygdala transcriptome and socioemotional behavior in rats exposed to valproic acid prenatally".
Tian et al; 2014; Journal of Pineal Research, vol. 56, No. 1, pp. 1-11 "Melatonin reverses the decreases in hippocampal protein serine/threonine kinases observed in an animal model of autism".
AU Examination Report No. 1 dated May 27, 2021.
CN Office Action mailed Feb. 3, 23.
JP 1st Office Action mailed Aug. 17, 2021.
JP 2nd Office Action mailed May 11, 22.
KR Office Action Aug. 16, 2021.

* cited by examiner

BIOMARKER ASSAY FOR USE IN MONITORING AUTISM

FIELD OF THE INVENTION

The present invention relates to a biomarker assay for use in monitoring autism spectrum disorders (ASD), in particular ASD phenotype 1. Furthermore, the assay of the invention is also useful for diagnosing ASD phenotype 1.

BACKGROUND OF THE INVENTION

The cAMP-dependent protein kinase (PKA) is activated by the binding of cAMP to the regulatory subunit (R), of the molecule and results in the release of the active catalytic kinase subunit (C). Most of the effects of cAMP in eukaryotic systems are the result of phosphorylation of proteins at serine or threonine residues by PKA. There are several isoforms of both subunits of PKA. PKA is localized subcellularly by binding to multidomain scaffolding proteins known as AKAPs which bind to the R subunits of the holoenzyme (Pearce, L. R., D. Komander, and D. R. Alessi, The nuts and bolts of AGC protein kinases. Nat Rev Mol Cell Biol, 2010. 11 (1): p. 9-22). PKA plays a key role in neurodevelopment.

Autism spectrum disorder (ASD) is a group of neurodevelopmental disorders frequently characterized by impairments in social interactions, difficulties with language and communication, and the presence of repetitive, perseverative behaviors (Abrahams B S, Geschwind D H; Advances in autism genetics: on the threshold of a new neurobiology; Nat Rev Genet. 2008 June; 9(6):493), (Zoghbi H Y, Bear M F; Synaptic dysfunction in neurodevelopmental disorders associated with autism and intellectual disabilities; Cold Spring Harb Perspect Biol. 2012 Mar. 1; 4(3)). Characteristic symptoms or behavioral traits of ASD typically appear during the first three years of life and remain present throughout life in the vast majority of patients. Intensity of symptoms may vary from patient to patient and may decrease as the patient develops adaptive skills. Environmental factors, Developmental (transition to puberty . . . ) or comorbidities such as epilepsia can also result in a worsening of symptoms.

According to the fifth edition of the diagnostic and statistical manual of mental disorders (DSM. 5th Edition. Washington, DC: American Psychiatric Association; 2013. American Psychiatric Association. Diagnostic and Statistical Manual of Mental Disorders), ASD is characterized by two sets of core impairments: persisting deficits of social communication and interaction and restricted and repetitive behaviors, interests, activities. Compared to the previous edition (DSM-IV-Text Revision) (DSM-IV-TR 4th Edition. Washington, DC: American Psychiatric Association; 2000. American Psychiatric Association. Diagnostic and Statistical Manual of Mental Disorders.) DSM-5 introduced significant changes. In the diagnostic criteria, language abilities not employed in social communication have been de-emphasized. Further, the diagnostic subcategories, namely autistic disorder, Asperger disorder, Rett disorder, childhood disintegrative disorder, and pervasive developmental disorder (PDD) not otherwise specified are now encompassed by the diagnostic criteria for autism spectrum disorder. DSM-5 additionally requires to specify where patient fits within three levels of increasing severity of ASD, from (1) ("requiring support") to (2) ("requiring substantial support") up to (3) ("requiring very substantial support").

Other related behaviorally based definitions for Autism are proposed under various terminologies in other diagnostic manuals and classification system including the WHO-ICD-10 definition of Autistic Disorder (2017/18 ICD-10-CM Diagnosis Code F84.0)(World Health Organization. (1992). The ICD-10 classification of mental and behavioral disorders: Clinical descriptions and diagnostic guidelines. Geneva: World Health Organization).

Evidence has recently accumulated to support the theory that the ever-expanding number of ASD susceptibility genes could in fact converge towards a limited number of molecular pathways. This growing assumption offers important translational opportunities as genes mediating synaptic and circuit formation or synaptic transmission are also involved in other physiological processes including modulation of the adaptive and innate immune response (Myka L. Estes M L, McAllister A K (2015), Nature Reviews Neuroscience 16, 469-486), cell proliferation, survival and protein synthesis (Subramanian M, Timmerman C K, Schwartz J L, Pham D L and Meffert M K (2015), Front. Neurosci. 9:313. Tang G. et al. (2014), Neuron. 83, 1131-1143).

However, there is a growing recognition by the scientific community that the behavioral based DSM-5 diagnosis of ASD does not allow for reasonable classification in terms of molecular and genetic alterations, but rather serves as a behavior based umbrella term for a large group of disorders with different etiology. These differences are caused by specific variations in genetic alterations and gene expression patterns.

Attempts have been previously made to stratify ASD patients into smaller, more homogeneous subgroups by utilizing specific genetic signatures (Bernier et al; Disruptive CHD8 mutations define a phenotype of autism early in development; Cell 2014 Jul. 17; 158 (2): 263-276) or behavioral and clinical endophenotypes (Eapen V. and Clarke R. A.; Autism Spectrum Disorder: From genotypes to phenotypes: Front Hum Neurosci. 2014; 8:914). However, these strategies face difficulty encompassing the genetic and phenotypic heterogeneity of ASD, and may not assist in the identification of specific neurobiological pathways underlying disease.

Assays on a molecular basis might provide a way to classify ASD patients or monitor the course of their disease. However, because of the intrinsic complexity of ASD—and the complex intertwining of genetic and environmental causal factors, specific biomarkers for ASD have yet to be identified which could be used to establish such an assay.

Objective Problem to be Solved

The problem to be solved is thus the provision of means to efficiently and easily identify phenotypes of ASD patients and monitor the activity of their disease with the help of easy-to-use biomarker assays.

SUMMARY OF THE INVENTION

The present invention solves this problem by providing protein kinase A for use in diagnosing autism spectrum disorder (ASD) phenotype 1 in an ASD patient wherein protein kinase A levels are measured in a sample of the patient and wherein ASD phenotype 1 is diagnosed if the measured protein kinase A levels are lower than protein kinase A levels in an age and sex-matched control sample.

Likewise, the problem is solved by protein kinase A for use in monitoring variation in ASD severity in an ASD patient, wherein protein kinase A levels are measured in a sample of the patient and wherein an increase in ASD severity is characterized by a decrease of protein kinase A levels compared to protein kinase A levels measured in previous samples of the patient.

Thirdly, the problem is solved by a method for diagnosing ASD phenotype 1 in an ASD patient, the method comprising providing a sample of the patient, and measuring protein kinase A levels in the sample, and diagnosing ASD phenotype 1 if the protein kinase A levels measured in the sample are lower than protein kinase A levels in an age- and sex-matched control sample.

Furthermore, the problem is solved by a method for monitoring variation in ASD severity in an ASD phenotype 1 patient, the method comprising providing a sample of the patient, and measuring protein kinase A levels in the sample.

Lastly, the problem is solved by a method for monitoring efficacy of an ASD treatment in an ASD phenotype 1 patient, the method comprising providing a sample of the patient, and measuring protein kinase A levels in the sample.

DETAILED DESCRIPTION

In one aspect, the present invention relates to protein kinase A for use in diagnosing autism spectrum disorder (ASD) phenotype 1 in an ASD patient wherein protein kinase A levels are measured in a sample of the patient and wherein ASD phenotype 1 is diagnosed if the measured protein kinase A levels are lower than protein kinase A levels in an age and sex-matched control sample.

As used herein, the term autism spectrum disorder (ASD) is understood to cover a family of neurodevelopmental disorders characterized by deficits in social communication and interaction and restricted, repetitive patterns of behavior, interests or activities. In the following, the terms “autism spectrum disorder”, “autism” and “ASD” are used interchangeably.

The person skilled in the art is well aware of how a patient may be diagnosed with ASD. For example, the skilled person may follow the criteria set up in “American Psychiatric Association; Diagnostic and Statistical Manual of Mental Disorders (DSM-5) Fifth edition” to give a subject a diagnosis of ASD. Likewise, ASD patients may have been diagnosed according to standardized assessments tools including but not limited to DSM IV, ICD-9, ICD-10, DISCO, ADI-R, ADOS, CHAT.

In other cases, patients may have a well-established DSM-1V diagnosis of autistic disorder, Asperger’s disorder, or pervasive developmental disorder not otherwise specified (PDD-NOS).

Protein kinase A is a family of cAMP-dependent protein kinases consisting of two catalytic and two regulatory subunits. As understood herein, the term “protein kinase A” covers any member of this enzyme family. In particular, the term is understood to refer to the two major types of mammalian protein kinase A, type I and type II (PKA I and PKA II). These kinases are distinguished by the presence of different R subunits termed RI and RII. Through biochemical studies and gene cloning, three isoforms of the C subunit, Cα, Cβ, and Cγ, and four isoforms of the R subunits, RIα, RIβ, RIIα, and RIIβ, have been identified. The present invention envisages not only measurement of holoenzyme of protein kinase A, but also of each of the subunits. In a preferred embodiment isoenzyrne protein kinase A located in serum is measured.

Measurement of protein kinase A can be performed using any method known to the skilled person. Examples of measurement methods include immunoassays, immunofluorescence assays, enzyme-linked immunosorbent assays (ELISA), lateral flow assays, radioimmunoassays (RIA) and magnetic immunoassays (MIA). In a preferred embodiment, protein kinase A levels are measured using a modified MESACUP Protein Kinase A Activity Assay. In another preferred embodiment, protein kinase A levels are measured by ELISA using an anti-protein kinase A-antibody.

The sample of the patient may be any sample of a body fluid. In a preferred embodiment, the sample is selected from a blood sample, serum sample, plasma sample, saliva sample, a urine sample. The sample may have been processed to facilitate measurement of protein kinase A, e.g., by purification or by separation of individual components in the case of a whole-blood sample.

The term “age and sex-matched control sample” refers to a sample taken from an individual or a group of healthy subjects having an age and sex corresponding to the ASD patient. In order to perform the present invention, it is not necessary measure protein kinase A levels of the control sample anew each time the present invention is performed. Instead, the present invention envisages the possibility to compare the measured value for protein kinase A levels of the respective ASD patient to mean reference values which have been determined for a large cohort group.

The present invention is useful for diagnosing ASD phenotype 1 in ASD patients. ASD phenotype 1 patients can be defined by the following clinical signs and symptoms: having: 1) at least 1 mandatory characteristics: enlarged head size versus control population characterized by at least one standard deviation above the mean head circumference (HC) at 24 months and/or formal macrocephaly (HC>97% of the general population) and/or cyclical aggravation of core or ancillary autism symptoms potentiated by periods of infectious events, deciduous tooth loss, post-traumatic injury, endogenous and exogenous temperature variation; 2) and at least 2, most preferably at least 3 of the following 20 characteristics: accelerated hair and nail growth versus control population; Increased tendency to present with lighter colors of skin and eyes as compared to individuals of the same ethnicity; Substantially longer eyelashes than control subjects of the same ethnicity; At least 5 non-contiguous areas of hypopigmented skin, particularly presenting on the back of the patient; Signs of edema during periods of infectious events, deciduous tooth loss, post-traumatic injury, or endogenous and exogenous factors modifying body temperature; more specifically, facial edema located in the periorbital and forehead areas; Increased blood levels of gamma-glutamyl transpeptidase (GGT) as compared to typically developing individuals of the same age and ethnicity; Congenital genitourinary malformations and/or functional impairment to initiate urinating; Hypoplasia of the patella; Frequent episodes of diarrhea specifically before the age of 5 years; Frequent episodes of tinnitus; Thinning of the corpus callosum; Positive family history for hematological malignancies in particular but not limited to myeloma and acute promyelocytic leukemia; Positive family history for rheumatoid arthritis, that is at least two affected first-degree relatives in two consecutive generations; Adverse events in response to acetyl-salicylic acid or its derivatives; Iris coloboma, either monolateral or bilateral; Sleep hyperhidrosis particularly in newborns, toddlers and young children (notably increased night sweating during infancy and childhood-often reported by relatives to requires bed linen changes); Increased Th1/Th2 ratio (i.e. elevated levels of Interleukin 1 beta, Interleukin 6, TNF-alpha, Interferon gamma); Congenital accessory or duplicated spleen; Congenital absence of the cisterna chyli; Reported history of mother suffering from viral or bacterial infection during pregnancy and/or biologically confirmed Maternal immune activation during pregnancy.

Likewise, ASD phenotype 1 patients can be characterized by upregulation of Nrf2 transcriptional factor and clinical signs of heightened expression of proliferation-associated pathways. At the same time, these patients show an upregulation of pathways involved in in adaptation to stress, apoptosis or cell differentiation, cell proliferation, cell cycle progression, cell division and differentiation (in particular but not limited to PI3K, AKT, mTOR/MAPK, ERK/JNK-P38).

In this phenotype of patients, proinflammatory cytokines (TNF-α, IL-6, IL-1β, IL-17A, IL-22 and GM-CSF), Th1 cytokine (INF-γ) and chemokine (IL-8) may be significantly increased in the brain compared to healthy control patients. Th2 cytokines (IL-4, IL-5 and IL-10) may not show a significant difference. The Th1/Th2 ratio may be significantly increased in phenotype 1 patients.

While the above clinical signs and symptoms provide a hint for the presence of ASD phenotype 1 in an ASD patient, the present invention provides for the first time a biomarker that can be used to identify and/or diagnose ASD phenotype 1 in an ASD patient. Consequently, the present invention provides a fast and easy method for the identification of ASD phenotype 1 patients.

In another embodiment, the present invention also relates to protein kinase A for use in monitoring variation in ASD severity in an ASD patient, wherein protein kinase A levels are measured in a sample of the patient and wherein an increase in ASD severity is characterized by a decrease of protein kinase A levels compared to protein kinase A levels measured in previous samples of the patient.

In a preferred embodiment, the present invention provides protein kinase A for use in monitoring variation in ASD severity in an ASD phenotype 1 patient. In addition to the methods according to the present invention, ASD phenotype 1 patients may also be identified with the help of a challenge test as described in PCT/EP2018/080372. Briefly, the concept of a challenge test is based on administration of an Nrf2-activator to an ASD patient. In ASD phenotype 1 patients, who already show an upregulation of the respective pathways, further activation of Nrf2 will lead to a worsening of core symptoms. Consequently, ASD phenotype 1 patients may be identified by a negative response in a challenge test.

Another way of identifying ASD phenotype 1 patients is to check for upregulation of Nrf2. The person skilled in the art is well aware of how upregulation of a specific gene such as Nrf2 may be checked. For example, it may be checked on the mRNA level using quantitative PRC techniques such as qPCR or RT-qPCR. Likewise, upregulation of a gene may be determined on the protein level using protein quantification techniques such as Western Blot and quantitative dot blots. Upregulation is understood to mean an increase of mRNA levels or protein levels of at least 20% when compared to samples from healthy subjects.

Variation in ASD severity is herein defined as the variation in severity of both ASD core and ancillary symptoms in a patient, which may be caused by fever, environmental factors such as temperature changes, infections, or allergic episodes. ASD core symptoms include but are not limited to social-interaction difficulties, communication challenges and a tendency to engage in repetitive behavior. ASD ancillary symptoms include but are not limited to intellectual disability, learning disability, genitourinary organ dysfunction (i.e. impairment to initiate urinating), episodes of diarrhea.

In ASD phenotype 1 patients, an increase in ASD severity is accompanied and, in some cases, preceded by a decrease in protein kinase A levels. Consequently, the present invention is useful for monitoring variations in ASD severity in ASD patients, preferably in ASD phenotype 1 patients, by measuring protein kinase A levels in a sample of the patient, wherein an increase in ASD severity is characterized by lower levels of protein kinase A compared to protein kinase A levels measured in previous samples of the patient. In a preferred embodiment, monitoring of variation in ASD severity according to the present invention comprises measuring protein kinase levels in at least two samples of the ASD or ASD phenotype 1 patient.

In yet another embodiment, the present invention relates to protein kinase A for use in monitoring efficacy of an ASD treatment in an ASD phenotype 1 patient, wherein protein kinase A levels are measured in a sample of the patient and wherein a positive response to the ASD treatment is characterized by an increase of protein kinase A levels in comparison to baseline protein kinase A levels of the patient prior to treatment.

The present invention is useful for monitoring efficacy of an ASD treatment in ASD phenotype 1 patients. In ASD phenotype 1 patients, successful and effective treatment of ASD will increase levels of protein kinase A. Consequently, a positive response to the treatment is characterized by an increase of protein kinase A levels in comparison to baseline protein kinase A levels of the patient prior to treatment. An insufficient response is characterized by the absence of an increase of and a cessation of response is characterized by a decrease in protein kinase A levels compared to levels of protein kinase A measured in the patient during a positive response. Depending on whether a positive response or an insufficient response or a cessation of response is determined in the patient, treatment may be maintained in the case of a positive response or may be increased in case of an insufficient response or cessation of response. In the case of an insufficient response or cessation of response, treatment may also be replaced with a different treatment.

As used herein, the term "ASD treatment" refers to any treatment for ASD known to the skilled person. Examples of ASD treatment include administration of risperidone, aripiprazole, clozapine, haloperidol, sertraline, oxytocin, secretin, methylphenidate, venlafaxine, fluoxetine, citalopram, bumetanide, memantine, rivastigmine, mirtazapine, melatonin, acamprosate, atomoxetine, intrathecal baclofen, DMXB-A (a derivative of the nemertine toxin anabasein), EPI-743: vincerinone, RG7314: antagonist of the V1A vasopressin receptor, sulforaphane, suramin. Additionally, possible treatments to be monitored with the present invention can be found in EP18204763.9.

In another embodiment, the present invention relates to a method for diagnosing ASD phenotype 1 in an ASD patient, the method comprising providing a sample of the patient, and measuring protein kinase A levels in the sample, and diagnosing ASD phenotype 1 if the protein kinase A levels measured in the sample are lower than protein kinase A levels in an age- and sex-matched control sample.

In yet another embodiment, the present invention relates to a method for monitoring variation in ASD severity in an ASD phenotype 1 patient, the method comprising providing a sample of the patient, and measuring protein kinase A levels in the sample.

In yet another embodiment, the present invention relates to a method for monitoring efficacy of an ASD treatment in an ASD phenotype 1 patient, the method comprising
providing a sample of the patient, and
measuring protein kinase A levels in the sample.

In another embodiment, the present invention provides a kit for use in diagnosing ASD phenotype 1 in an ASD patient, the kit comprising means to measure protein kinase A levels in a sample of the patient.

In yet another embodiment, the present invention provides a kit for use in monitoring ASD disease activity in an ASD phenotype 1 patient, the kit comprising means to measure protein kinase A levels in a sample of the patient.

In another embodiment, the present invention provides a kit for use in monitoring efficacy of an ASD treatment in an ASD phenotype 1 patient, the kit comprising means to measure protein kinase A levels in a sample of the patient.

The means for measuring protein kinase A levels in a sample may for example comprise anti-protein kinase A-antibodies. Additionally, the kit according to the present invention may also comprise suitable buffers, detection agents and charts with reference values.

Example

Serum samples from three patients with ASD (diagnosed based on DSM-5 criteria) were collected at two different points. The first round of serum samples was collected prior to treatment and represented baseline values prior to treatment. The second round of serum samples were collected after 1 month of treatment, wherein ibudilast at a total dosage of 0.6 mg/kg 3 times/day was administered in conjunction with bumetanide at a total daily dosage of 0.08 mg/kg administered in two daily intakes.

Protein kinase A levels of serum samples were measured using the MESACUP Protein Kinase Assay Kit (Medical & Biological laboratories CO., LTD) The assay was conducted according to the specification provided by the manufacturer.

Three patients were classified as ASD Phenotype 1 is they showed:

at least 1 mandatory characteristics:
- enlarged head size versus control population characterized by at least one standard deviations above the mean head circumference at 24 months and/or formal macrocephaly (HC>97% of the general population) and/or
- cyclical aggravation of core or ancillary autism symptoms potentiated by periods of infectious events, deciduous tooth loss, post-traumatic injury, endogenous and exogenous temperature variation and at least 2, and most preferably at least 3 of the following 20 characteristics:
- Accelerated hair and nail growth versus control population
- Increased tendency to present with lighter colors of skin and eyes as compared to individuals of the same ethnicity
- Substantially longer eyelashes than control subjects of the same ethnicity
- At least 5 non-contiguous areas of hypopigmented skin, particularly presenting on the back of the patient
- Signs of edema during periods of infectious events, deciduous tooth loss, post-traumatic injury, or endogenous and exogenous factors modifying body temperature; more specifically, facial edema located in the periorbital and forehead areas
- Increased blood levels of gamma-glutamyl transpeptidase (GGT) as compared to typically developing individuals of the same age and ethnicity
- Congenital genitourinary malformations and/or functional impairment to initiate urinating
- Hypoplasia of the patella
- Frequent episodes of diarrhea specifically before the age of 5 years
- Frequent episodes of tinnitus
- Thinning of the corpus callosum
- Positive family history for hematological malignancies in particular but not limited to myeloma and acute promyelocytic leukemia
- Positive family history for rheumatoid arthritis, that is at least two affected first-degree relatives in two consecutive generations
- Adverse events in response to acetyl-salicylic acid or its derivatives
- Iris coloboma, either monolateral or bilateral
- Sleep hyperhidrosis particularly in newborns, toddlers and young children (notably increased night sweating during infancy and childhood—often reported by relatives to requires bed linen changes)
- Increased Th1/Th2 ratio (i.e. elevated levels of Interleukin 1 beta, Interleukin 6, TNE-alpha, Interferon gamma)
- Congenital accessory or duplicated spleen
- Congenital absence of the cisterna chyli
- Reported history of mother suffering from viral or bacterial infection during pregnancy and/or biologically confirmed Maternal immune activation during pregnancy Results of the assay are presented below in table 2.

TABLE 2

PKA measurement before and after treatment with ibudilast at a total dosage of 0.6 mg/kg 3 times/day in conjunction with bumetanide at a total dosage of 0.08 mg/kg 2 times/day

| PKA value | Patient 1 | Patient 3 | Patient 4 |
|---|---|---|---|
| Before treatment (claim 3) | 3.9 ng/ml | 5 ng/ml | 5.1 ng/ml |
| After treatment (claim 3) | 12.4 ng/ml | 14.8 ng/ml | 14.8 ng/ml |

The invention claimed is:

1. A method of treatment comprising:
providing a sample of bodily fluid from a patient,
measuring protein kinase A levels in the sample,
identifying the patient as being an autism spectrum disorder (ASD) phenotype 1 if the protein kinase A levels measured in the sample are lower than protein kinase A levels in an age- and sex-matched control sample, and
treating the patient by administering a therapeutically effective amount of ibudilast and bumetanide.

2. The method according to claim 1, wherein the sample is selected from a blood sample, serum sample, plasma sample, saliva sample and a urine sample or any other body fluid sample.

* * * * *